(12) United States Patent
Flynn et al.

(10) Patent No.: US 6,590,116 B1
(45) Date of Patent: Jul. 8, 2003

(54) PROCESS FOR PURIFYING SILOXANE

(75) Inventors: Joseph S. Flynn, Painted Post, NY (US); Dale R. Powers, Painted Post, NY (US); Brian P. Strines, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/423,727

(22) Filed: Oct. 1, 2001

Related U.S. Application Data

(60) Provisional application No. 60/044,687, filed on Apr. 18, 1997.

(51) Int. Cl.[7] .............................. C07F 7/08; C08G 79/12; C03B 19/06; C03B 19/14
(52) U.S. Cl. .......................... 556/460; 528/31; 528/10; 528/502; 423/336; 65/60.52
(58) Field of Search ............................. 556/460; 528/31, 528/10, 502; 423/336; 65/60.52; 422/255, 291

(56) References Cited

U.S. PATENT DOCUMENTS 5,043,002 A * 8/1991 Dobbins et al. ............ 423/336

\* cited by examiner

*Primary Examiner*—Paul F. Shaver
(74) *Attorney, Agent, or Firm*—Robert L. Carlson

(57) ABSTRACT

The present invention is directed to a process for purifying siloxane. The invention relates to a method of making a purified siloxane feedstock for use in the manufacturing of silica glass. The invention further relates to solid phase extracting impurities from a polyalkylsiloxane starting material.

32 Claims, 7 Drawing Sheets

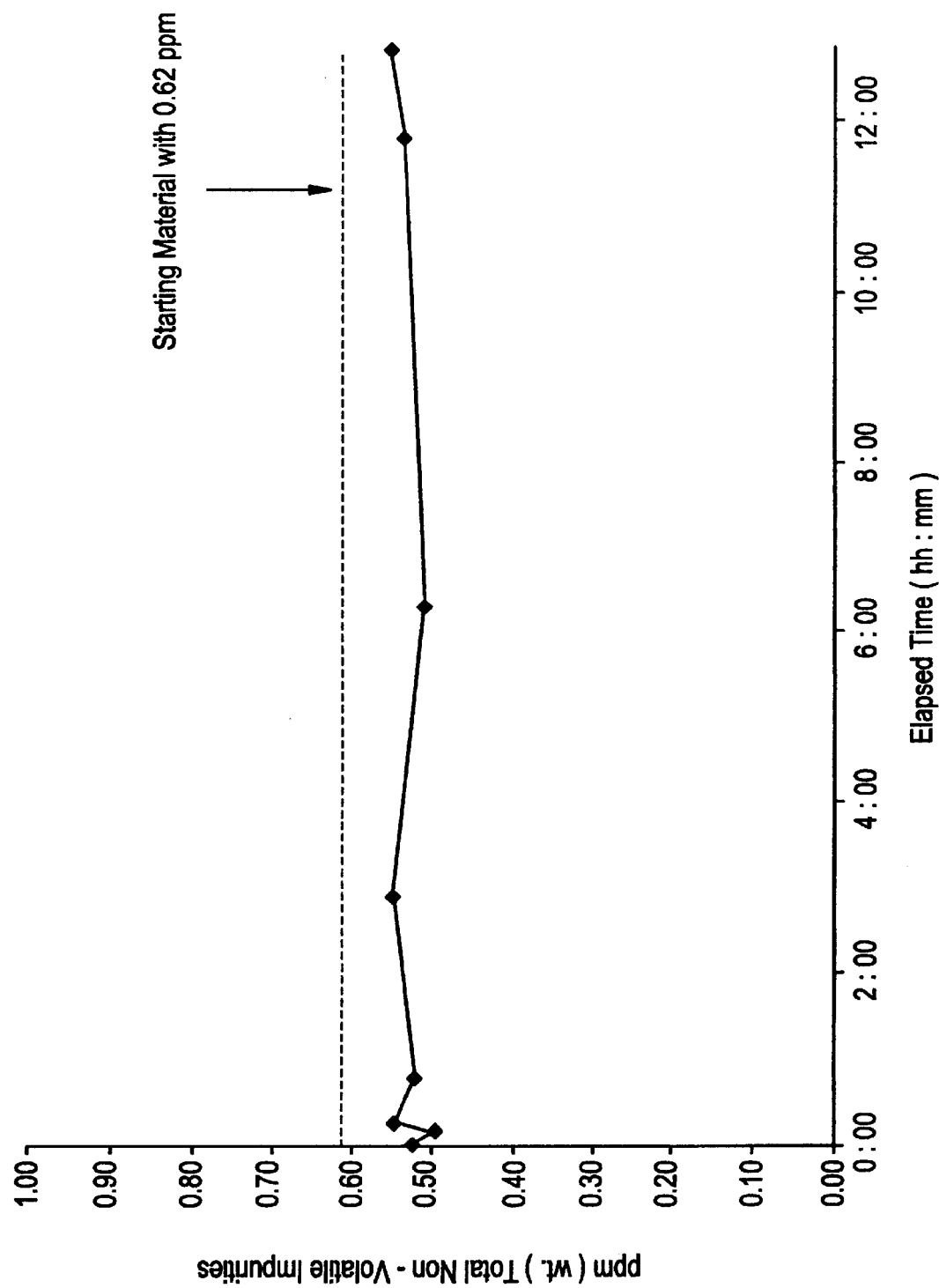

PROCESS FOR PURIFYING SILOXANE

This application claims priority to U.S. patent application Ser. No. 60/044687 filed on Apr. 18, 1997, the content of which is herein incorporated by reference.

FIELD OF THE INVENTION

The present invention relates to a method of purifying a siloxane compound. More particularly, the present invention relates to a method of making a purified siloxane feedstock for use in the manufacturing of silica glass.

BACKGROUND OF THE INVENTION

There are various processes that involve the production of silica glass from reactants containing silicon. Such processes include a feedstock containing silicon and a means for transporting the feedstock to a conversion site where the feedstock is converted into silica. An apparatus used in such a process usually consists of a liquid feedstock reservoir, a means of converting said liquid feedstock into a vapor and delivering the vaporized feedstock to a burner where the feedstock is converted by flame hydrolysis into silica soot. Silica soot produced by such a burner is then collected on a deposition surface. Such collected silica may be simultaneously or subsequently heat treated to form a fused non-porous transparent high purity silica glass article, particularly well suited for optical applications.

Historically, silicon tetrachloride has been used as the main silicon containing feedstock that is converted to silica. This use presents disadvantages in that environmentally unsafe HCl is produced as a byproduct. As an alternative to using silicon tetrachloride as a feedstock, silica may be formed from halide-free, silicon-containing feedstocks such as siloxanes. U.S. Pat. No. 5,043,002 to Dobbins et al., the disclosure of which is hereby incorporated by reference, discloses the use of siloxane feedstocks. U.S. Pat. No. 5,043,002 to Dobbins et al. discloses the benefits of using polyalkylsiloxanes such as polymethylsiloxanes, and in particular polymethylcyclosiloxanes with octamethylcyclotetrasiloxane as the preferred silicon-containing feedstock, in the manufacturing of silica glass.

It has been found that the use of such siloxane feedstocks, and in particular octamethylcyclotetrasiloxane, in the manufacture of silica glass poses problems caused by the siloxanes' tendency to polymerize and form higher molecular weight siloxanes which form polymeric deposits such as gels under the conditions and environments of the silica glass manufacturing process. Siloxane feedstocks form troublesome polymeric compounds which deposit in the vaporization, delivery, and conversion equipment used in the silica glass manufacturing process. This polymerizing of the siloxane feedstock causes manufacturing difficulties due to the clogging and restriction of the feedstock flow during storage, vaporization, delivery and conversion. These deposits create great difficulty in controlling, monitoring, and metering the amount and rate at which the siloxane feedstock is utilized in the silica glass manufacturing process and also gel globs which spew out of the burner may produce inhomogeneities which would produce defects in the silica glass.

U.S. patent application Ser. No. 08/574,961 by Henderson and Powers, the disclosure of which is hereby incorporated by reference, discloses a method of purifying polyalkylsiloxanes by removing impurities having boiling points greater than 250° C. by distillation in order to avoid the problem of polymeric deposits and gel formation when using the purified polyalkylsiloxane as a siloxane feedstock in the silica manufacturing process.

SUMMARY OF INVENTION

Accordingly, the present invention is directed to a method of making a high purity polyalkylsiloxane that substantially obviates one or more of the problems due to limitations and disadvantages of the related art.

Additional features and advantages of the invention will be set forth in the description which follows, and in part will be apparent from the description, or may be learned by practice of the invention. The objectives and other advantages of the invention will be realized and attained by the processes, apparatuses, and compositions particularly pointed out in the description and claims.

To achieve these and other advantages and in accordance with the purpose of the invention, as embodied and broadly described, the invention includes the method of making a high purity nonpolar polyalkylsiloxane. This method includes the step of providing a refined polyalkylsiloxane starting material which has polar impurities and is made up of greater than 95% by weight of the nonpolar polyalkylsiloxane which is the polyalkylsiloxane target product of the invention. The method further includes the step of extracting the polar impurities from the starting material to produce a high purity nonpolar polyalkylsiloxane product.

In another aspect, the invention includes a method of making a polymeric deposit inhibited siloxane feedstock which is resistant to polymer formation and not prone to form polymeric deposits. This method includes the steps of providing a starting siloxane feedstock which has polymeric deposit forming impurities and then solid phase extracting the polymeric deposit forming impurities from the starting siloxane feedstock in order to produce a polymeric deposit inhibited siloxane feedstock.

It is to be understood that both the foregoing general description, and the following detailed description are exemplary and explanatory and are intended to produce further explanation of the invention as claimed.

The accompanying drawings are included to provide a further understanding of the invention and are incorporated in and constitute a part of this specification, illustrate embodiments, and aspects of the invention and together with the description serve to explain the principle of the invention.

BRIEF DESCRIPTION OF THE DRAWINGS

FIG. 6 is a plot of total non-volatile impurities versus elapsed time of a solid phase extraction process run in accordance with the teachings of the present invention.

DETAILED DESCRIPTION OF THE INVENTION

Figure 1:
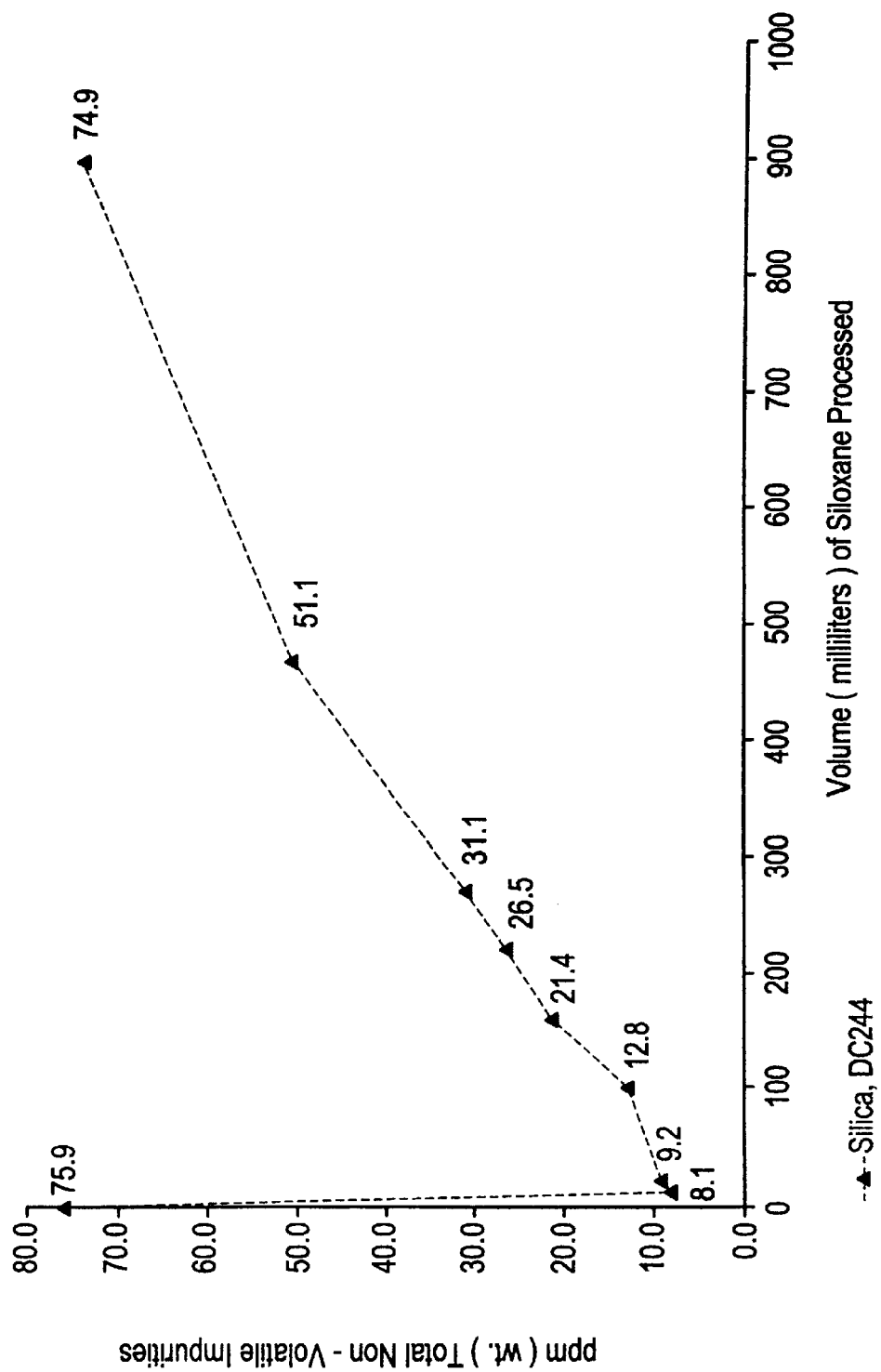
FIG. 1 is a plot of total non-volatile impurities versus volume of siloxane fluid processed in accordance with the teachings of the present invention.

The invention provides a convenient, efficient, and economical means of making a purified nonpolar polyalkylsiloxane. Reference will now be made in detail to the present preferred embodiments of the invention. The inventive method of making a purified nonpolar polyalkylsiloxane includes the step of providing a refined polyalkylsiloxane starting material. The polyalkylsiloxane starting material has been refined so that greater than 95% of it by weight is a nonpolar polyalkylsiloxane, which is the target product compound to be obtained by the invention. The greater than 95% polyalkylsiloxane starting material includes unwanted and problematic polar impurities.

The method of the invention, further includes the step of extracting these polar impurities from the polyalkylsiloxane starting material to produce a high purity nonpolar polyalkylsiloxane product. The step of extracting the polar impurities includes solid phase extracting said polar impurities. With solid phase extraction, the polar impurities are removed from the liquid polyalkylsiloxane starting material using a solid absorbent bed. Solid phase extracting the polar impurities includes selectively absorbing the polar impurities out of the liquid starting material and into the solid absorbent bed. The preferred method of solid phase extracting the polar impurities is to contact the starting material with a silica gel absorbent bed.

A high purity nonpolar polyalkylsiloxane is the targeted product of the invention, and it is preferred to provide a starting material comprised of greater than 98% by weight of the nonpolar polyalkylsiloxane, and more preferably greater than 99% by weight.

The preferred nonpolar polyalkylsiloxane of the invention is a cyclic polyalkylsiloxane, more preferably a cyclic polymethylsiloxane. The most preferred polyalkylsiloxane of the invention is octamethylcyclotetrasiloxane.

The invention further includes providing a refined volatile polyalkylsiloxane starting material containing greater than 70 ppm of total non-volatile impurities which includes the polar impurities and solid phase extracting a sufficient amount of the polar impurities to produce a volatile high purity nonpolar polyalkylsiloxane product containing less than 30 ppm of the total non-volatile impurities, and more preferably less than 10 ppm of the total non-volatile impurities, and most preferably less than 1 ppm of the non-volatile impurities. The preferred method of measuring the total non-volatile impurity concentration level is with an Evaporative Light-Scattering Detector (ELSD) such as the Alltech Varex MKIII brand ELSD commercially available from Alltech Associates Inc. of Deerfield, Ill. along with the Alltech 426 HPLC brand pump and the Alltech 570 brand Autosampler. A sample of the polyalkylsiloxane to be measured for total non-volatile impurities is nebulized with a pressurized gas such as nitrogen, and the nebulized sample is passed through the detector, which is connected to the pump. The drift tube of the light-scattering detector, which is provided with a laser light source, is maintained at about 65–85° C., preferably about 75° C. The laser light scattered by the particulates in the nebulized sample is detected, and an analog signal proportional to the light intensity is generated and detected. The detector response is a peak that can be displayed with a chart recorder or a chromatographic integrator. Either peak height or area may be used for quantification of the response. Area integration is preferred, and the area under the peak is approximately directly proportional to the concentration of the total non-volatile impurities contained in the polyalkylsiloxane sample. The non-volatile characteristics at the impurities is measured in comparison to the volatility of the targeted polyalkylsiloxane product of the inventive process. For example, the ELSD is calibrated so that the volatility of the targeted polyalkylsiloxane product such as octamethylcyclotetrasiloxane gives no signal. A percentage of the total non-volatile impurities measured in the polyalkylsiloxane sample are the polar impurities which may be solid phase extracted. A majority of the measured total non-volatile impurities are high molecular weight siloxanes impurities.

The inventive method of purifying a siloxane is particularly suited for making a polymeric deposit inhibited siloxane feedstock. The inventive method produces a siloxane feedstock particularly well suited for use in the manufacturing of silica glass. The use of siloxane feedstocks in the manufacturing of silica glass products such as fused silica glass and optical waveguides is plagued with problems related to the siloxane's tendency to polymerize and form deposits comprised of higher molecular weight species. Such siloxane formed polymeric deposits cause production, maintenance, and related clogging problems in the manufacturing of silica glass, particularly in the siloxane feedstock delivery and conversion steps. The invention includes a method of making a polymeric deposit inhibited siloxane feedstock and the polymeric deposit inhibited siloxane feedstock product made therefrom.

The method of making a polymeric deposit inhibited siloxane feedstock includes the steps of providing a starting siloxane feedstock containing a polymeric deposit forming impurity and solid phase extracting the polymeric deposit forming impurity from the starting siloxane feedstock to produce a polymeric deposit inhibited siloxane feedstock. Solid phase extracting the polymeric deposit forming impurities from the starting feedstock is accomplished by contacting the starting siloxane feedstock in liquid form with a silica gel absorbent which selectively extracts the polymeric deposit forming impurities out of the liquid siloxane feedstock.

It is preferred that the starting siloxane feedstock containing polymeric deposit forming impurities is comprised at least 99% by weight of a siloxane.

This method is particularly beneficial in removing polar polymeric deposit forming impurities from the nonpolar siloxane feedstock. It is preferred to remove silanol terminated siloxanes, which are polymeric deposit forming impurities having hydroxy ends, by contact with a polar absorbent bed material such as silica gel.

The method of making a polymeric deposit inhibited siloxane feedstock is very useful in the manufacturing and making of silica glass, which may further comprise vaporizing the polymeric deposit inhibited siloxane feedstock to form a vapor feedstock, and delivering the feedstock to a conversion site, such as a flame hydrolysis burner, where the feedstock is converted into $SiO_2$ soot which is deposited and consolidated to form silica glass articles, such as optical waveguide preforms and optical fiber.

Commercially available polyalkylsiloxane compositions, such as GE Silicones SF1173 brand silicone fluid and DOW CORNING® 244 Fluid, when used as siloxane feedstocks in the silica glass manufacturing process tend to form troublesome polymeric deposits which impede and interrupt the silica glass manufacturing process. In addition, it has been found that the purified polyalkylsiloxane products produced in accordance with U.S. patent application Ser. No. 08/574,961 by Henderson and Powers may still form troublesome polymeric deposits during the silica glass manufacturing process. It has been discovered that the above refined starting polyalkylsiloxanes feedstocks contain polar impurities which contribute to the formation of polymeric deposits and that these polar impurities can be effectively and efficiently removed from the feedstocks by solid phase extraction, preferably utilizing a silica gel absorbent bed. These starting siloxane feedstocks still contain impurities in their refined states which contribute to the formation of troublesome polymeric deposits. These siloxane feedstocks contain polar impurities which have boiling points close to the boiling point of the targeted siloxane product, which makes it particularly difficult to remove such impurities by distillation methods since this depends on differences in boiling points between the targeted product and the unwanted impurity.

It has been found advantageous to extract such difficult to distill polymeric deposit forming impurities based on the difference in polarity between the impurities and the targeted siloxane feedstock molecules. Targeted polyalkylsiloxane feedstock molecules such as octamethylcyclotetrasiloxane are nonpolar compared to polar polymeric deposit forming impurity molecules such as hydroxyl end capped siloxane molecules.

It was surprising and unexpected that such near target product boiling point impurities would contribute to the polymeric deposit forming problems in the silica manufacturing process since their boiling point and vaporization characteristics are close to equal of the targeted polyalkylsiloxane feedstock product's boiling point and vaporization characteristics. Such polar impurities are present in distilled and refined polyalkylsiloxane starting compositions at sufficiently low concentrations relative to their vapor pressure that they should be able to be used in the silica manufacturing process in that they will vaporize within a few degrees of the boiling point of targeted polyalkylsiloxane feedstock material. These impurities should not recondense to form troublesome polymeric deposits because they are present in low concentrations and their dew points are about the same as the targeted polyalkylsiloxane feedstock material which is present in large concentration throughout the silica manufacturing process. But these impurities, particularly polar impurities, do contribute to polymeric deposit formation in the silica glass manufacturing process in that they undergo chemical reactions to form troublesome polymeric deposits prior to being delivered to the conversion site burner flame where they would be converted into silica soot. Such polar impurities, particularly hydroxyl end capped molecules, undergo chemical reactions with themselves or other molecules to form polymeric compounds which are deposited in the components of the silica manufacturing process. In the silica glass manufacturing process such impurities may form polymeric deposits which do not typically cause severe problems in the vaporizer due to the large size of its passages but such polymeric deposits are very troublesome in the small diameter conduits and passages of the vapor delivery system such as the vapor delivery tube of the burner and lead to flow inconsistencies and non-uniform silica glass soot preform deposition. U.S. Pat. No. 5,599,371 by Cain, Powers, et al., the disclosure of which is herein incorporated by reference, discloses a precision burner in which polymeric deposits may form which require interruption of the silica manufacturing process so that the troublesome polymeric deposits can be removed.

EXAMPLE 1

DOW CORNING® 244 octamethylcyclotetrasiloxane fluid comprised of at least 96% by weight of octamethylcyclotetrasiloxane was passed through a selection of solid absorbent beds to determine which solid absorbent bed would be the most effective in purifying the siloxane feedstock by solid phase extraction. Samples of DOW CORNING® 244 octamethylcyclotetrasiloxane fluid were passed through 300 mg Maxi-Clean™ Cartridges commercially available from Alltech Associates Inc. of Deerfield, Ill. Cartridges of silica gel (Alltech Associates Inc. Catalog No. 20986) extracted 89% of the total non-volatile impurities present in the fluid. Cartridges of DiOL (Alltech Associates Inc. Catalog No. 210080) extracted 86% of the total non-volatile impurities present in the fluid. Cartridges of Cyano (CN Alltech Associates Inc. Catalog No. 210030) extracted 82% of the total non-volatile impurities present in the fluid. Cartridges of C18 (Alltech Associates Inc. Catalog No. 20938) extracted 63% of the total non-volatile impurities present in the fluid. Cartridges of alumina ($Al_2O_3$ Alltech Associates Inc. Catalog No. 210095) extracted 62% of the total non-volatile impurities present in the fluid.

Based on this comparison, silica gel is the preferred solid phase extraction absorbent bed. During solid phase extraction of impurities from a liquid, silica gel absorbs polar molecules from the liquid in contact with it. Silica gel absorbent beds have a vast network of interconnected microscopic pores whose surface attract and hold polar molecules by physical absorption and capillary condensation. Silica gel's ability to absorb materials is highest for polar molecules, and a more polar molecule will tend to displace a less polar molecule. It has been found that silica gel is able to effectively remove polar impurities from nonpolar polyalkylsiloxanes and is the preferred solid phase extraction absorbent bed.

EXAMPLE 2

The capacity of a silica gel absorbent bed to remove polar impurities from refined polyalkylsiloxane was determined to be that approximately one gram of silica gel could effectively purify one liter of refined polyalkylsiloxane. DOW CORNING® 244 octamethylcyclotetrasiloxane was contacted with a 300 mg Maxi-Clean™ silica gel cartridge, while the purity and cumulative volume of the exiting octamethylcyclotetrasiloxane was measured as shown in FIG. 1. As increasing amounts of polar impurities are absorbed by the silica gel, the silica gel becomes less effective at removing the impurities. If breakthrough is defined as the point when the exit concentration of impurities is half of the original concentration of impurities then silica gel had a breakthrough capacity of 300 ml for the 300 mg of silica gel (liter per gram). The DOW CORNING® 244 sample had an original concentration of 75.9 ppm by weight of total non-volatile impurities prior to contacting the silica gel.

EXAMPLE 3

Polar non-volatile impurities, a majority of which were high molecular weight siloxane impurities, were solid phase extracted from DOW CORNING® 244 octamethylcyclotetrasiloxane liquid according to Table 1.

TABLE 1

| | Liquid Input Total Non-Volatile | Liquid Output Total Non-Volatile |
| --- | --- | --- |

| Silica Gel Absorbent Bed | Liquid Flowrates Used | Impurity (by weight) | Impurity (by weight) |
|---|---|---|---|
| 4.5 grams Grade 408 Davisil (brand) 12/28 Mesh particle size | 4 g/min | 81 ppm | 64–80 ppm |
| 4.3 grams Alltech brand #5650 40/60 Mesh particle size | 2 g/min | 78 ppm | 13.7–71 ppm |
| 2 grams Alltech brand #1457 250–400 microns particle size 150 Å pore size | 1.65–3 g/min | 75.4 ppm | 7–27 ppm |
| 2 grams Alltech brand #1415 250–400 microns particle size 60 Å pore size | 0.65–3.75 g/min | 74 ppm | 6.7–22 ppm |

This showed that small particle size silica gels are more effective at removing polar impurities from siloxane feedstocks than larger particle sizes. The silica gels with 200–400 micron particle sizes were about as effective as the Maxi-Clean™ silica gel cartridges used in Examples 1 and 2 which had silica gel particle sizes in the 10–100 micron range.

This also showed that smaller particle sizes in the 200–400 micron range are preferred for increased flowrates because the reduced particle size reduces the absorption path between and within the silica gel particle and allows for high flux rates.

EXAMPLE 4

Figure 2:
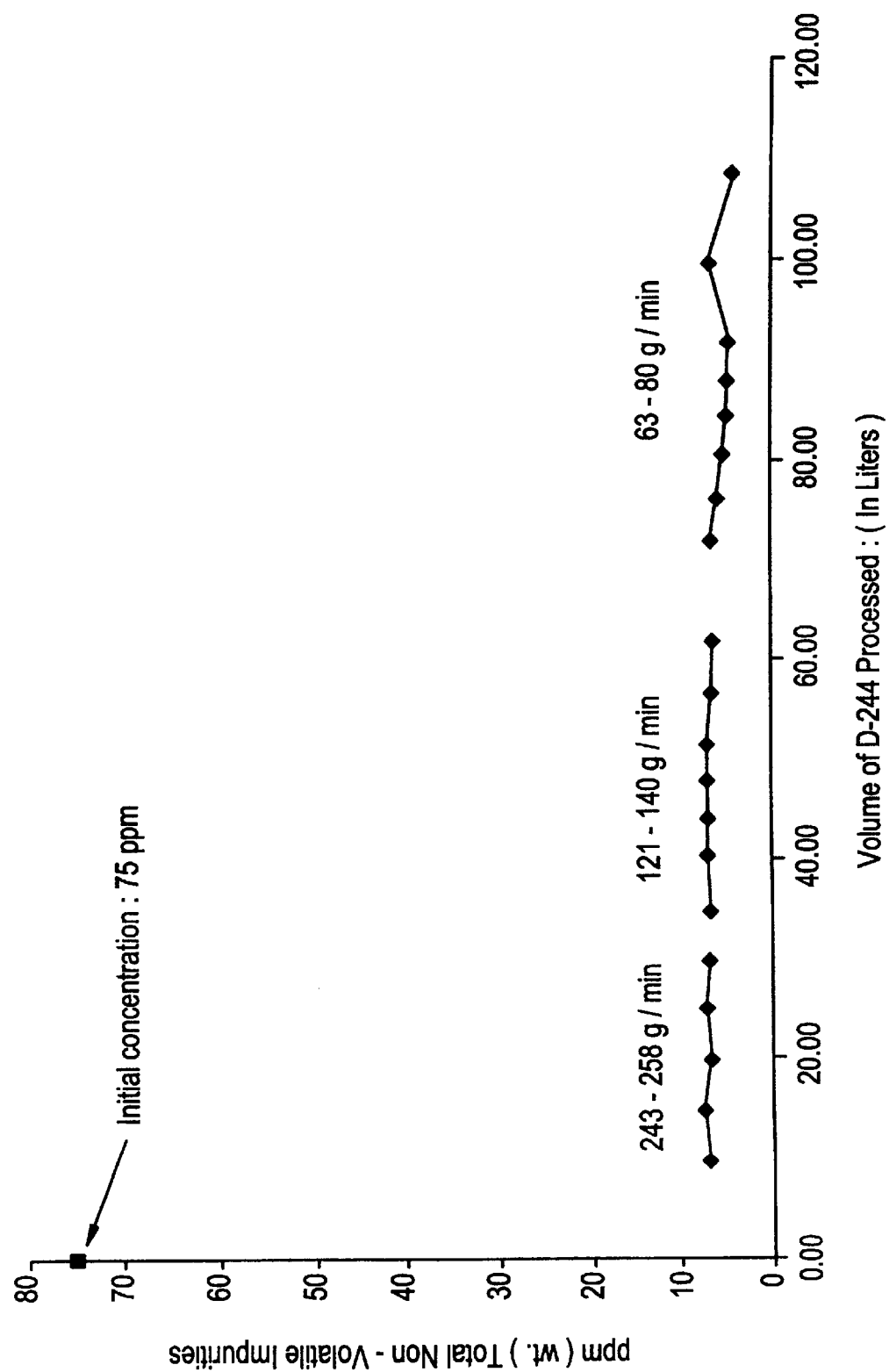
FIG. 2 is a plot of total non-volatile siloxane impurities versus volume of siloxane fluid processed in accordance with the teachings of the present invention.
Figure 3:
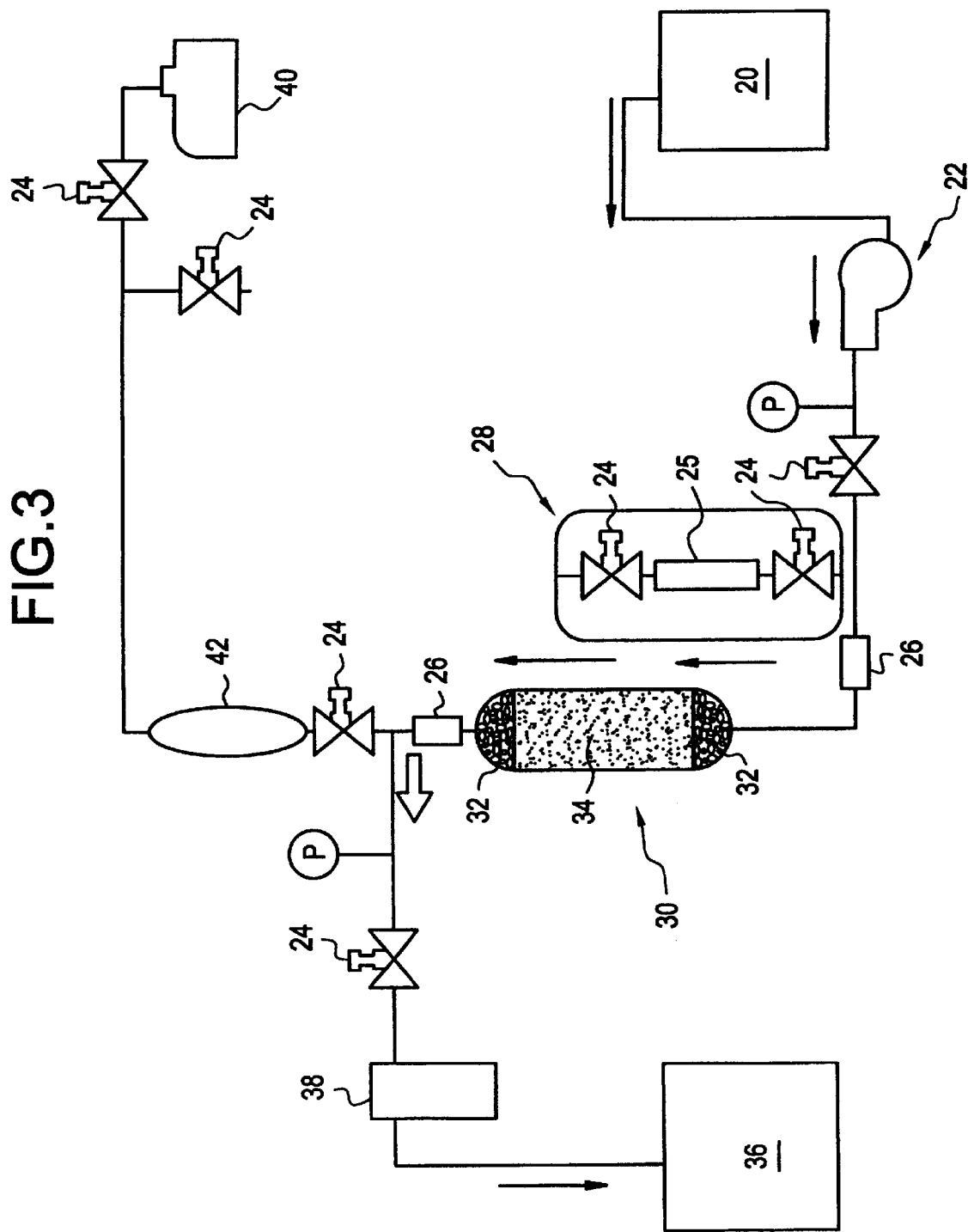
FIG. 3 comprises a schematic representation of the method and apparatus set up of the invention.
Figure 4A:
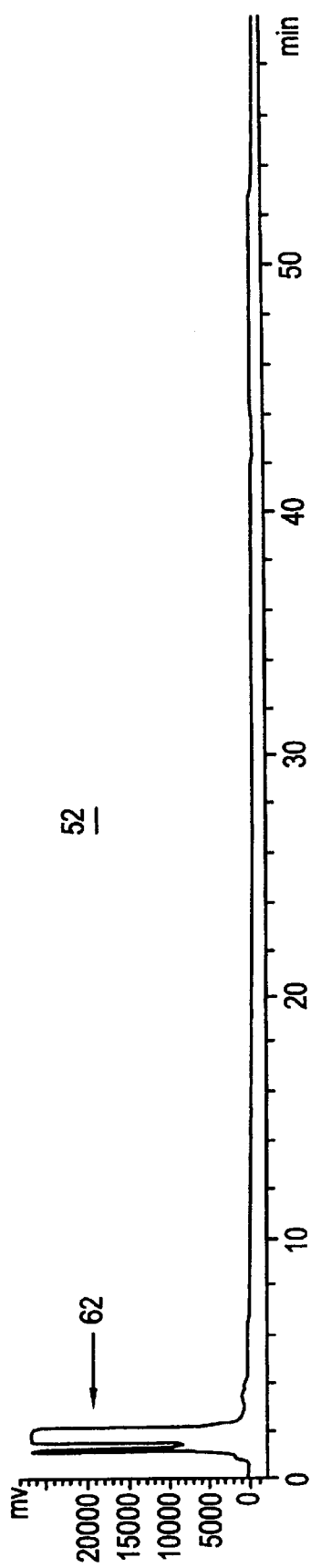
FIG. 4 comprises HPLC chromatograms disclosing the extraction of polar impurities from siloxane in accordance with the teachings of the invention.
Figure 4B:
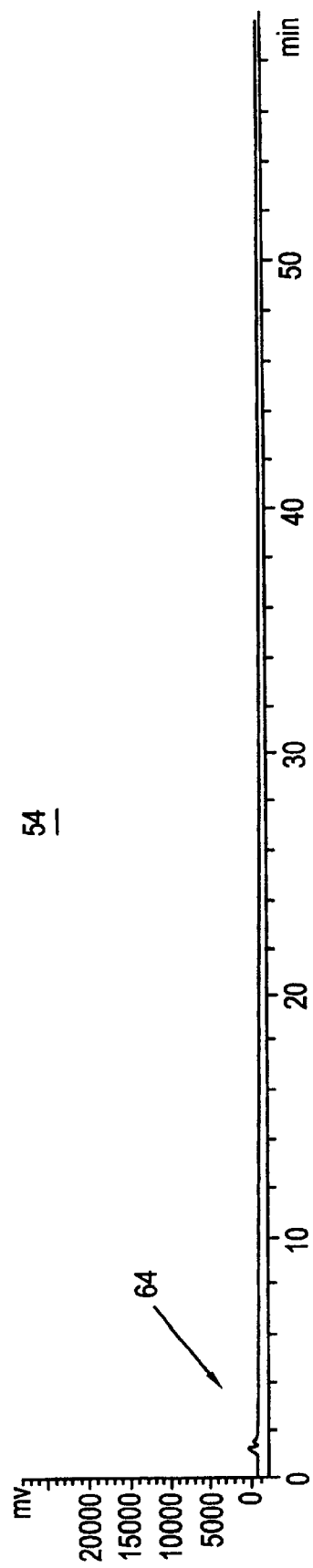
Figure 4C:
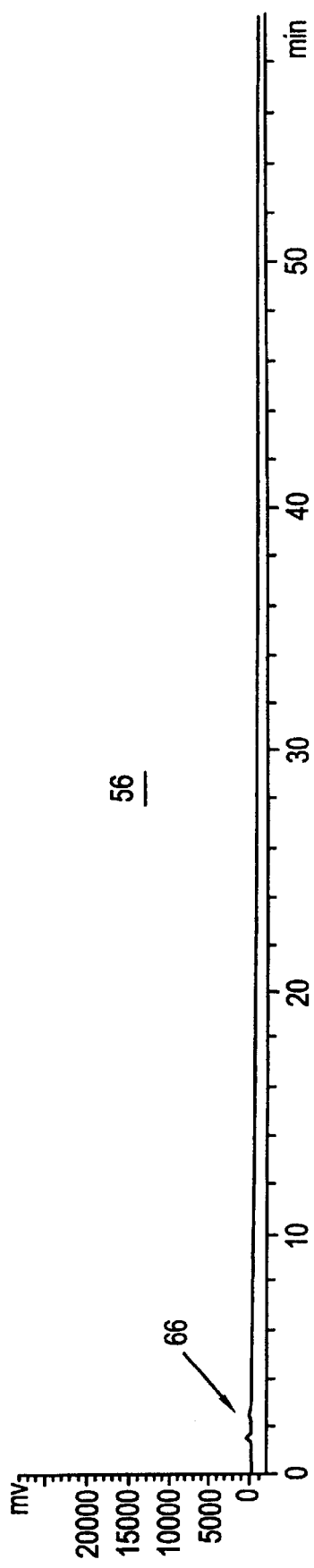
Figure 4D:
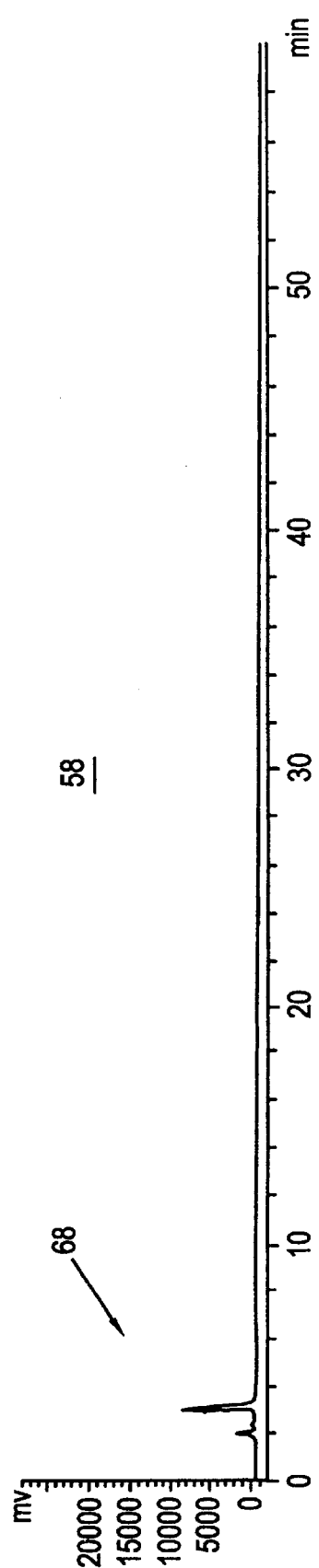

800 grams of Alltech Silica Gel brand #1457 having a pore size of 150 Å and a particle size of 200–400 microns as put in a 2250 ml Matheson gas sample cylinder, and about 5 cm thick layers of 4 cm diameter glass beads were placed at the entrance and exit of the cylinder to allow the siloxane liquid to flow more readily at the tapered entrance and exit to form a solid phase extraction column such as silica gel column 30 in FIG. 3. A total of about 108 liters of DOW CORNING® 244 octamethylcyclotetrasiloxane having an original total non-volatile impurity concentration of 75 ppm by weight was flowed through this silica gel bed. FIG. 2 shows the results of this solid phase extraction with the accumulated volume given along the X-axis and the concentration of total non-volatile impurities given along the Y-axis in ppm. The siloxane liquid first had a flowrate in the range of 243–258 grams/minute, which was reduced to a range of 121–140 grams/minute after about 35 cumulative liters, which was then reduced to 63–80 grams/minute after about 61 cumulative liters. This solid phase extraction system was of sufficient size to efficiently remove polar non-volatile impurities, which included high molecular weight siloxane impurities at flowrates over 250 grams/minute and had the capacity to remove polar impurities from over 100 liters of refined polyalkylsiloxane starting material to produce a high purity nonpolar polyalkylsiloxane product.

EXAMPLE 5

Polar impurities were solid phase extracted from a refined polyalkylsiloxane starting material of a purified polyalkylsiloxane composition in accordance with U.S. patent application Ser. No. 08/574,961 (herein incorporated by reference) comprised of at least 99.5% by weight of octamethylcyclotetrasiloxane and having a total concentration of less than about 2 ppm of impurities having boiling points, under atmospheric conditions, of greater than about 250° C. and containing some impurities having molecular weights of less than about 250 grams/mole using silica gel to produce a polymeric deposit inhibited silica forming feedstock. This octamethylcyclotetrasiloxane liquid was distilled and refined in accordance with U.S. patent application Ser. No, 08/574,961 to have a minimal amount of high boiling impurities with boiling points greater than about 250° C. Such a refined octamethylcyclotetrasiloxane liquid in which impurities with boiling points greater than about 250° C. have been removed by distillation, have been found to form troublesome polymeric deposits in the silica glass manufacturing process and particularly in high production volume fiber optic preform lathes, though to a lesser degree than DOW CORNING® 244 octamethylcyclotetrasiloxane silica forming feedstock. Alltech Associates Inc. 646 Series brand silica gel with a 200–400 microns particle size and 150 Å pore size (Alltech Associates Inc. Catalog No. 1457) was used as the silica gel absorbent bed.

FIG. 3 is a schematic drawing of the silica gel solid phase extraction system used. Refined polyalkylsiloxane starting material container 20 is used to store the octamethylcyclotetrasiloxane liquid starting siloxane feedstock which contained polymeric deposit forming impurities. Container 20 is connected by a liquid conduit to siloxane feedstock controllable flow rate pump 22. Valves 24 control the flow of gasses and siloxane liquid through the system. Pump 22 delivers starting siloxane feedstock through conduits to air trap 28 and filter 26. Starting siloxane feedstock flows through a conduit from filter 26 to solid phase extracting silica gel absorbent bed column 30. Air trap 28 is comprised of valves 24 and vertical fluid holding column 25 and is used to prevent gas bubbles from reaching silica gel column 30. Filter 26 is a 90 micron filter which filters the starting siloxane feedstock prior to reaching silica gel column 30 and keeps the silica gel in the column. Silica gel column 30 is comprised of a glass cylinder container having a hemispherical top and bottom. Glass beads 32 which have 3–5 mm diameters fill the hemispherical top and bottom of column 30 in order to distribute the siloxane feedstock uniformly across the silica gel absorbent bed 34.

Silica gel absorbent bed 34 is formed by packing approximately 0.9 kg of silica gel particles into column 30. Prior to contacting the siloxane starting material with silica gel bed 34, silica column 30 is activated by heating the silica column to about 270–295° C. to remove absorbed water and improve the silica column's capacity for extracting polar impurities from the siloxane feedstock.

In use, starting siloxane feedstock liquid flows through column 30 which extracts polar and polymeric deposit forming impurities from the liquid feedstock to produce a high purity nonpolar polymeric deposit inhibited siloxane feedstock product which is delivered to polyalkylsiloxane product storage container 36 via liquid conduits. Particulate filter 38 catches and retains particles which may escape from column 30.

Vacuum pump 40 is used in the filing of silica column 30 with the starting siloxane material and to purge and remove gas and bubbles from the solid phase extraction system to improve liquid flow and ensure efficient contact between the liquid and the solid absorbent bed. Degassing chamber 42 assists the vacuum pump in the removal of unwanted gasses from the silica column and overall system.

Approximately 110 gallons of octamethylcyclotetrasiloxane liquid starting material was provided by container 20 which consisted of two 55 gallon drums used in succession. The polar impurities in this starting material were extracted using this silica gel solid phase extraction system. The high purity nonpolar octamethylcyclotetrasiloxane feedstock product from which the polar impurities were extracted was collected in container 36 which consisted of two 55 gallon drums filled in succession.

Figure 5:
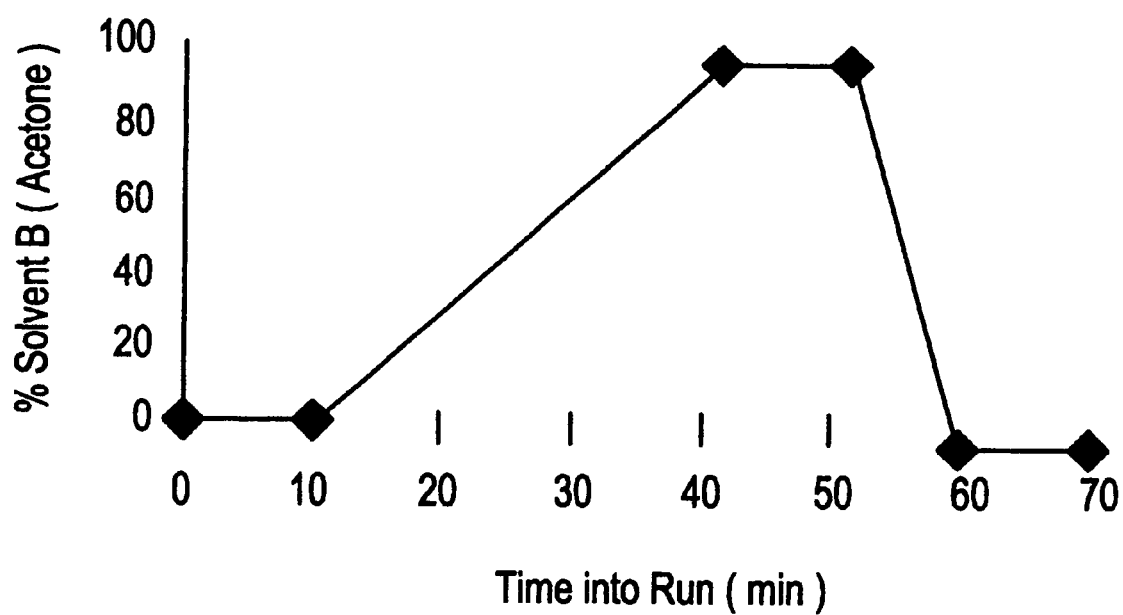
FIG. 5 discloses the Gradient Elution Program utilized in the HPLC Analysis of siloxane in accordance with the teaching of the invention.

The results of this solid phase extracted are shown in the chromatograms of FIG. 4. Chromatogram 52 is a chromatogram of a sample of the octamethylcyclotetrasiloxane liquid starting material. Chromatogram 54 is a chromatogram of a sample of the high purity nonpolar octamethylcyclotetrasiloxane feedstock product taken after 2 gallons had been solid phase extracted. Chromatogram 56 is a chromatogram of a sample of the high purity nonpolar octamethylcyclotetrasiloxane feedstock product taken after 55 gallons had been solid phase extracted. Chromatogram 58 is a chromatogram of a sample of the high purity nonpolar octamethylcyclotetrasiloxane feedstock product taken after 110 gallons had been solid phase extracted. The chromatograms of FIG. 4 are of the acetone fractions from the extraction of 4 liters of each sample. The chromatograms of FIG. 4 were done with HPLC (high performance liquid chromatography) Analysis using a Base Deactivated C-18, 3 $\mu$m, 3.2×150 mm Column and a flow rate of 0.75 ml/min. A gradient using solutions A (90:10, Acetone:Water) and B (100% Acetone) was utilized in accordance to FIG. 5. High polar impurities were present in the starting material as indicated by the high peaks 62 of HPLC chromatogram 52. Low peaks 64, 66, and 68 respectively of HPLC chromatograms 54, 56, and 58 show that these polar impurities were removed by this solid phase extraction process.

Comparison of the HPLC chromatograms shows that solid phase extraction is able to remove polar impurities from refined polyalkylsiloxane starting materials having very low levels of total non-volatile impurities (about 1 ppm), solid phase extraction of such refined polyalkylsiloxane starting materials may remove at least 50% of the polar impurities present in the starting material, preferably at least 80% of the polar impurities present in the starting material, more preferably at least 90% of the polar impurities present in the starting material, and most preferably substantially all (at least 99%) of the polar impurities present in the starting material.

The first 55 gallons of high purity nonpolar octamethylcyclotetrasiloxane product produced by this solid phase extraction was used as a polymeric deposit inhibited siloxane in the silica manufacturing process for making silica glass preforms for optical fibers. This high purity nonpolar octamethylcyclotetrasiloxane feedstock was vaporized then delivered to the conversion site burners of a high production volume optical fiber preform lathe where the vapor was converted by flame hydrolysis into silica soot which was deposited to form a preform. This solid phase extraction octamethylcyclotetrasiloxane feedstock preformed well without the problematic formation of polymeric deposit, compared to previous uses of the refined polyalkylsiloxane starting material which had not been solid phase extracted and which did not preform well and formed troublesome polymeric deposits particularly in the vapor delivery systems, burner fume tubes, and the burner orifices.

Such a solid phase extraction system provides a convenient and economical means of obtaining polymeric deposit inhibited siloxane feedstocks for conversion into silica glass products, particularly when compared to expensive and complicated distillation processes.

EXAMPLE 6

Polar non-volatile impurities were extracted from 55 gallons of refined polyalkylsiloxane octamethylcyclotetrasiloxane starting material as used in Example 5 using a Biotage, Inc. (Charlottesville, Va.) Flash 75L brand radial compression module (cartridge housing, part # SF-002-19071) loaded with a Biotage, Inc. pre-packed KP-SIL brand silica gel cartridge (part # FKO-1107-19073). The silica bed was a total charge of 800 grams, with a particle size range of 32–63 microns, a 60 Å pore size, and a surface area of 500–550 m$^2$/g silica.

Preparation consisted of flushing the silica gel cartridge with 7 liters of HPLC grade hexane at flow rates varying between 26–120 ml/min followed by 8 liters of HPLC grade acetone at 75 ml/min, then a final flush with 8 liters of hexane at 75 ml/min. One liter of octamethylcyclotetrasiloxane was then pumped through the cartridge to purge the hexane from the silica gel bed. An initial sample was taken from the octamethylcyclotetrasiloxane starting material (later determined to have a total non-volatile impurity content of 0.62 ppm by weight). The solid phase extraction process was begun with the pump set to deliver octamethylcyclotetrasiloxane starting material at a flow rate of 250 ml/min. Column backpressure of the cartridge was 70 psig. Table 3 and FIG. 6 show when 20 ml samples of the octamethylcyclotetrasiloxane solid phase extraction product were taken, as well as the total non-volatile impurity content, determined at a later time, for each of these samples.

TABLE 3

| (hh:mm) | Time | | | | | | | |
|---|---|---|---|---|---|---|---|---|
| | 00:00 | 00:10 | 00:15 | 00:47 | 02:56 | 06:20 | 11:50 | 12:50 |
| | Total Non-Volatile Impurity Content (by weight) | | | | | | | |
| (ppm) | 0.52 | 0.50 | 0.55 | 0.52 | 0.55 | 0.51 | 0.54 | 0.56 |

This shows that the total non-volatile impurity content was reduced by roughly 13% through extraction of polar species by solid phase extraction and that processing of a refined polyalkylsiloxane starting material having a total non-volatile impurity content of greater than 0.56 ppm by weight (about 0.62 ppm) can reduce the total non-volatile impurity content to less than 0.56 ppm. Following the extraction of 55 gallons of the octamethylcyclotetrasiloxane starting fluid, the silica cartridge was flushed with 8 liters of hexane followed by 8 liters of acetone at a flow rate of 75 ml/min. Both fractions were rotary evaporated down to approximately 30 ml. The acetone fraction was dark yellow in color.

In practicing the invention, silica gel particle sizes from about 10 $\mu$m to 5 mm are preferred, silica gel particle sizes from about 25 $\mu$m to 250 $\mu$m are more preferred, and silica gel particle sizes from about 40 $\mu$m to 100 $\mu$m are most preferred. Silica gel pore sizes from about 40–300 Å are preferred, and silica gel pore sizes from about 60–200 Å are more preferred. It is preferred to use a silica bed mass to siloxane process volume of about 1 gram/100 liters, more preferably about 1 gram/10 liters, and most preferably about 1 mg/ml (1 gram/1 liter). It is preferred to use solid phase extraction flow rates of 2500 ml/min per 1 liter of bed volume and more preferrably 250 ml/min per 1 liter of bed volume (4 min contact time).

It will be apparent to those skilled in the art that various modifications and variations can be made in the present invention without departing from the spirit or scope of the invention. Thus, it is intended that the present invention cover the modifications and variations of this invention provided the come within the scope of the appended claims and their equivalents.

What is claimed:

1. A method of making a high purity nonpolar polyalkylsiloxane comprising:
    providing a refined polyalkylsiloxane starting material comprised by weight of at least 96% of a nonpolar polyalkylsiloxane, said starting material further comprised of polar impurities;
    extracting said polar impurities from said starting material to produce a high purity nonpolar polyalkylsiloxane product.

2. The method of claim 1, wherein said extracting said polar impurities comprises solid phase extracting said polar impurities.

3. The method of claim 1, wherein said extracting said polar impurities comprises contacting said starting material with a silica gel absorbent bed.

4. The method of claim 1, wherein providing a refined polyalkylsiloxane starting material further comprises providing a refined polyalkylsiloxane starting material comprised by weight of at least 98% of a nonpolar polyalkylsiloxane.

5. The method of claim 1, wherein providing a refined polyalkylsiloxane starting material further comprises providing a refined polyalkylsiloxane starting material comprised by weight of at least 99% of a nonpolar polyalkylsiloxane.

6. The method of claim 1, wherein providing a refined polyalkylsiloxane starting material further comprises providing a refined volatile polyalkylsiloxane starting material having a total non-volatile impurity concentration level greater than 70 ppm by weight which includes said polar impurities and wherein extracting said polar impurities produces a volatile high purity nonpolar polyalkylsiloxane product having a total non-volatile impurity concentration level less than 30 ppm by weight.

7. The method of claim 6, wherein extracting said polar impurities from said starting material comprises extracting said polar impurities from said starting material to produce a volatile high purity nonpolar polyalkylsiloxane product having a total non-volatile impurity concentration level less than 10 ppm by weight.

8. The method of claim 6, wherein extracting said polar impurities from said starting material comprises extracting said polar impurities from said starting material to produce a volatile high purity nonpolar polyalkylsiloxane product having a total non-volatile impurity concentration level less than 1 ppm by weight.

9. The method of claim 1, wherein providing a refined polyalkylsiloxane starting material further comprises providing a refined volatile polyalkylsiloxane starting material having a total non-volatile impurity concentration level greater than 30 ppm by weight which includes said polar impurities and wherein extracting said polar impurities produces a volatile high purity nonpolar polyalkylsiloxane product having a total non-volatile impurity concentration level less than 30 ppm by weight.

10. The method of claim 1, wherein providing a refined polyalkylsiloxane starting material further comprises providing a refined volatile polyalkylsiloxane starting material having a total non-volatile impurity concentration level greater than 10 ppm by weight which includes said polar impurities and wherein extracting said polar impurities produces a volatile high purity nonpolar polyalkylsiloxane product having a total non-volatile impurity concentration level less than 10 ppm by weight.

11. The method of claim 5, wherein providing a refined polyalkylsiloxane starting material further comprises providing a refined volatile polyalkylsiloxane starting material having a total non-volatile impurity concentration level greater than 0.56 ppm by weight which includes said polar impurities and wherein extracting said polar impurities produces a volatile high purity nonpolar polyalkylsiloxane product having a total non-volatile impurity concentration level less than 0.56 ppm by weight.

12. The method of claim 5, wherein providing a refined polyalkylsiloxane starting material further comprises providing a refined volatile polyalkylsiloxane starting material having a total non-volatile impurity concentration level greater than about 1 ppm by weight which includes said polar impurities and wherein at least 80% by weight of said polar impurities are extracted.

13. The method of claim 12, which further includes extracting substantially all of said polar impurities.

14. The method of claim 5, wherein providing a refined polyalkylsiloxane starting material further comprises providing a refined polyalkylsiloxane starting material containing greater than 15 ppm of said polar impurities and extracting said polar impurities from said starting material to produce a high purity nonpolar polyalkylsiloxane product containing less than 10 ppm of said polar impurities.

15. The method of claim 14, wherein extracting said polar impurities from said starting material comprises extracting said polar impurities from said starting material to produce a high purity nonpolar polyalkylsiloxane product containing less than 5 ppm of said polar impurities.

16. The method of claim 1, wherein said nonpolar polyalkylsiloxane is a polymethylsiloxane.

17. The method of claim 1, wherein said nonpolar polyalkylsiloxane is a cyclic polyalkylsiloxane.

18. The method of claim 1, wherein said nonpolar polyalkylsiloxane is octamethylcyclotetrasiloxane.

19. A method of making a polymeric deposit inhibited siloxane feedstock comprising:
    providing a starting siloxane feedstock containing polymeric deposit forming impurities;
    solid phase extracting said polymeric deposit forming impurities from said starting siloxane feedstock to produce a polymeric deposit inhibited siloxane feedstock.

20. The method of claim 19, wherein providing a starting siloxane feedstock further comprises providing a starting siloxane feedstock comprised by weight of at least 99% of a siloxane.

21. The method of claim 9, wherein solid phase extracting said polymeric deposit forming impurities further comprises contacting said starting siloxane feedstock with a silica gel absorbent bed.

22. The method of claim 9, wherein said siloxane feedstock is octamethylcyclotetrasiloxane.

23. A method of making a high purity polymeric deposit inhibited octamethylcyclotetrasiloxane feedstock for manufacturing silica, comprising:
    providing a refined octamethylcyclotetrasiloxane starting liquid comprised by weight of at least 98% of octamethylcyclotetrasiloxane, said starting material containing polymeric deposit forming impurities;
    solid phase extracting said polymeric deposit forming impurities from said starting liquid to form a high purity polymeric deposit inhibited octamethylcyclotetrasiloxane feedstock for manufacturing silica.

24. The method of claim 23, wherein solid phase extracting said polymeric deposit forming impurities from said starting liquid further comprises contacting said starting liquid with a plurality of silica gel particles in a silica gel mass to starting liquid volume ratio of at least about 1 gram of silica gel to 1 liter of starting liquid.

25. A polymeric deposit inhibited siloxane feedstock comprised of at least 98% by weight of a siloxane molecule, wherein polar impurities contained in the feedstock have been solid phase extracted to below 30 ppm by weight.

26. The polymeric deposit inhibited siloxane feedstock of claim 25, wherein polar impurities contained in the feedstock have been solid phase extracted to below 15 ppm by weight.

27. The polymeric deposit inhibited siloxane feedstock of claim 26, wherein said feedstock is comprised of at least 99% by weight of a nonpolar siloxane molecule and polar impurities contained in the feedstock have been solid phase extracted to below 10 ppm by weight.

28. The polymeric deposit inhibited siloxane feedstock of claim 27, wherein polar impurities contained in the feedstock have been solid phase extracted to below 5 ppm by weight.

29. The polymeric deposit inhibited siloxane feedstock of claim 25, wherein polar impurities contained in the feedstock have been solid phase extracted from the feedstock into a silica gel.

30. A solid phase extracted high purity volatile siloxane silica producing feedstock comprised by weight of at least 98% octamethylcyclotetrasiloxane and containing less than 30 ppm by weight of polar non-volatile high molecular weight siloxane impurities.

31. An apparatus for purifying a silica glass forming siloxane feedstock comprised of:
   a means for providing a siloxane starting liquid; and
   a means for solid phase extracting impurities from said siloxane starting liquid.

32. An apparatus for manufacturing silica glass comprised of:
   a means for providing a siloxane starting liquid;
   a means for solid phase extracting impurities from said siloxane starting liquid; and
   a means for converting said siloxane starting liquid into silica glass.

* * * * *

UNITED STATES PATENT AND TRADEMARK OFFICE
CERTIFICATE OF CORRECTION

PATENT NO.      : 6,590,116 B1                                          Page 1 of 1
DATED           : July 8, 2003
INVENTOR(S)     : Flynn Joseph S. et al.

It is certified that error appears in the above-identified patent and that said Letters Patent is hereby corrected as shown below:

<u>Title page,</u>
Item [60], Related U.S. Application Data should read -- This application is a 371 of PCT/US98/07564 filed 04/14/1998, which claims benefit of Provisional application No. 60/044,687 filed on 04/18/1997. --

Item [56], References Cited, U.S. PATENT DOCUMENTS, insert
-- 5,312,947    5/1994    Tsukuno et al    556/456 --

Signed and Sealed this

Twenty-fifth Day of November, 2003

JAMES E. ROGAN
*Director of the United States Patent and Trademark Office*